(12) United States Patent
Herdina et al.

(10) Patent No.: US 11,471,630 B2
(45) Date of Patent: Oct. 18, 2022

(54) FLUID DISPENSING CATHETER

(71) Applicant: COVIDIEN LP, Mansfield, MA (US)

(72) Inventors: Katherine A. Herdina, Vallejo, CA (US); Thomas D. Magnuson, Philadelphia, PA (US)

(73) Assignee: COVIDIEN LP, Mansfield, MA (US)

( * ) Notice: Subject to any disclaimer, the term of this patent is extended or adjusted under 35 U.S.C. 154(b) by 559 days.

(21) Appl. No.: 16/513,861

(22) Filed: Jul. 17, 2019

(65) Prior Publication Data

US 2019/0336716 A1  Nov. 7, 2019

Related U.S. Application Data

(63) Continuation of application No. 15/584,561, filed on May 2, 2017, now Pat. No. 10,376,665.

(Continued)

(51) Int. Cl.
*A61M 16/04* (2006.01)
*A61M 25/00* (2006.01)
(Continued)

(52) U.S. Cl.
CPC .... *A61M 16/0484* (2014.02); *A61M 16/0463* (2013.01); *A61M 25/0068* (2013.01); *A61M 25/0082* (2013.01); *A61B 1/00089* (2013.01); *A61B 1/00137* (2013.01); *A61B 1/015* (2013.01); *A61M 16/0461* (2013.01); *A61M 25/0054* (2013.01); *A61M 25/0067* (2013.01);
(Continued)

(58) Field of Classification Search
CPC ...... A61M 16/0484; A61M 2025/0018; A61M 2025/0073; A61M 25/0067; A61M 25/0068; A61M 25/0082; A61M 16/0461; A61M 16/0463; A61M 2025/0096; A61M 25/0054; A61M 25/0097; A61B 1/00089; A61B 1/00137; A61B 1/015
See application file for complete search history.

(56) References Cited

U.S. PATENT DOCUMENTS 3,972,331 A    8/1976  Bolduc et al.
4,244,713 A *  1/1981  Goodwin ........... A61B 5/02042
                                              600/309

(Continued)

FOREIGN PATENT DOCUMENTS

| AU | 2015201947 A1 | 5/2015 |
| EP | 2508221 A1 | 10/2012 |
| JP | S5470893 A | 6/1979 |

OTHER PUBLICATIONS

Canadian Office Action dated Mar. 14, 2018, in Canadian Appln. No. 2,966,160.

(Continued)

*Primary Examiner* — Brandy S Lee
(74) *Attorney, Agent, or Firm* — Carter, DeLuca & Farrell LLP

(57) ABSTRACT

A fluid dispensing catheter includes an inner member defining a first passage and an outer member defining a second passage. The inner member is disposed within the second passage. The fluid dispensing catheter also includes a plug having a proximal section positioned within the first passage and a distal section extending distally from the proximal section. The distal section is positioned outside of the first passage and within the second passage.

20 Claims, 4 Drawing Sheets

Related U.S. Application Data

(60) Provisional application No. 62/332,073, filed on May 5, 2016.

(51) Int. Cl.
    *A61B 1/00*         (2006.01)
    *A61B 1/015*       (2006.01)

(52) U.S. Cl.
    CPC . *A61M 25/0097* (2013.01); *A61M 2025/0018* (2013.01); *A61M 2025/0073* (2013.01); *A61M 2025/0096* (2013.01)

(56) References Cited

U.S. PATENT DOCUMENTS

| | | | |
|---|---|---|---|
| 5,246,012 | A | 9/1993 | Strickland |
| 6,626,885 | B2 | 9/2003 | Massengale |
| 7,187,971 | B2 | 3/2007 | Sommer et al. |
| 8,152,755 | B1 * | 4/2012 | Wach ............... A61M 25/00 604/83 |
| 8,460,182 | B2 | 6/2013 | Ouyang et al. |
| 10,376,665 | B2 | 8/2019 | Herdina et al. |
| 2003/0051733 | A1 | 3/2003 | Kotmel et al. |
| 2007/0225682 | A1 | 9/2007 | Ash et al. |
| 2008/0097409 | A1 | 4/2008 | Stephens |
| 2009/0281376 | A1 | 11/2009 | Acosta et al. |
| 2011/0245665 | A1 | 10/2011 | Nentwick |
| 2012/0089101 | A1 * | 4/2012 | Carlyon ............... A61M 39/22 604/246 |
| 2013/0172677 | A1 | 7/2013 | Kennedy, II et al. |
| 2015/0057697 | A1 | 2/2015 | Carlstrom et al. |
| 2015/0272666 | A1 | 10/2015 | Wang |
| 2015/0320927 | A1 | 11/2015 | Nardeo |
| 2016/0000302 | A1 | 1/2016 | Brown et al. |
| 2016/0038007 | A1 | 2/2016 | Binmoeller et al. |

OTHER PUBLICATIONS

European Search Report dated Feb. 26, 2018 in EP Appln. No. 17191932.

Goldstein, et al. "Wedge Resection Margin Distances and Residual Adenocarcinoma in Lobectomy Specimens." Wedge Resection Margin Distances and Residual Adenocarcinoma in Lobectomy Specimens 120 (2003): 720-24. ASCP Journals. American Society forClinical Pathology, 2003.

Lung Cancer Structured Reporting Protocol. 2nd ed. Surry Hills, Australia: RCPA, 2013.

World Health Organization Classification of Tumours. Pathology and Genetics of Tumours of the Lung, Pleura, Thymus and Heart, vol. 10, 3rd edition, 2004.

European Search Report dated Oct. 11, 2017, issued in EP Application No. 17169402.

Australian Examination Report dated Jul. 5, 2018 in AU Appln. No. 2017203015.

European Examination Report issued in corresponding Appl. No. EP 17169402.9 dated Apr. 5, 2019 (4 pages).

* cited by examiner

FLUID DISPENSING CATHETER

CROSS REFERENCE TO RELATED APPLICATIONS

This application is a continuation of U.S. patent application Ser. No. 15/584,561, filed May 2, 2017, which claims the benefit of the filing date of provisional U.S. Patent Application No. 62/332,073, filed May 5, 2016, the entire contents of each of which are incorporated herein by reference.

FIELD

The present disclosure relates to surgical instruments and, more specifically, to catheters for dispensing fluids at a surgical site.

BACKGROUND

A common interventional procedure in the field of pulmonary medicine is bronchoscopy, in which a bronchoscope is inserted into the airways through the patient's nose or mouth. The structure of a bronchoscope generally includes a long, thin, flexible tube that typically contains three elements: an illumination assembly for illuminating the region distal to the bronchoscope's tip via an optical fiber connected to an external light source; an imaging assembly for delivering back a video image from the bronchoscope's distal tip; and a lumen or working channel through which instruments may be inserted, including but not limited to placement (e.g., guide wires), diagnostic (e.g., biopsy tools) and therapeutic (e.g., treatment catheters or laser, cryogenic, radio frequency, or microwave tissue treatment probes) instruments.

During particular procedures a catheter or extended working channel may be inserted through a working channel to enable navigation to sites too remote and having luminal diameters too small for the bronchoscope. An instrument may be inserted through the catheter or extended working channel in order to perform a procedure.

There is a need for an apparatus that facilitates controlled delivery of fluids to target locations beyond the distal tip of the bronchoscope.

SUMMARY

This disclosure relates generally to a fluid dispensing catheter defining a passage and a plug disposed within the passage to control flow of fluid from the catheter to a target within a surgical site. The plug is substantially cylindrical includes a flat that defines a gap with a surface defining the passage. The gap is sized such that flow of fluid from the passage through the gap is reduced and controllable by a clinician interfacing with the proximal portion of the catheter which is remote from the target.

In an aspect of the present disclosure, a fluid dispensing catheter includes an elongate body and a plug. The elongate body has a proximal portion and a distal portion with a passage defined between the proximal and distal portions. The plug has a proximal section that is positioned within the passage in the distal portion of the elongate body to partially occlude the passage. The plug being substantially cylindrical and having a flat parallel to and offset from a longitudinal axis of the plug. The flat defining a gap with the elongate body.

In aspects, the plug has a distal section that extends distally from the proximal section. The distal section may be positioned outside of the passage. The proximal section may have a first diameter and the distal section may have a second diameter that is larger than the first diameter.

In some aspects, the elongate body has an inner member and an outer member. The inner member may define the passage and the outer member may extend distally past the inner member. The distal portion may include a tip that is disposed over a distal end of the outer member. The tip may include a cap and an inner wall that defines a channel therebetween. The cap may define a tip opening that is in communication with the passage of the inner member. The distal end of the outer member may be received within the channel to secure the tip to the elongate member. The inner wall may define a tip passage that is in communication with the passage of the inner member. The plug may include a distal section that is disposed within the tip passage. The distal section may partially occlude the tip passage.

In certain aspects, the proximal portion includes a cover that is configured to seal the passage. The cover may define a septum that is configured to seal about instruments that are inserted into the passage through the cover. The cover may include a connector for sealingly attaching an instrument to the catheter that is in communication with the passage. The cover may include a plunger that has a disc disposed within the passage such that retraction of the disc draws fluid into the distal portion of the catheter and wherein extension of the disc expels fluid from within the distal portion of the catheter.

In another aspect of the present disclosure, a method of delivering fluid to target locations within a patient includes positioning a distal portion of a fluid dispensing catheter adjacent a target location within a patient and manipulating a proximal portion of the catheter which is disposed external to the patient to expel fluid from within the distal portion of the catheter. The catheter has an inner member that defines a passage. The distal portion includes a plug that partially occludes the passage of the catheter. The plug may have a flat that defines a gap with the inner member such that fluid is expelled from the distal portion in a controlled manner.

In aspects, manipulating the proximal portion may include inserting a syringe through a cover of the proximal portion of the catheter to expel fluid from the distal portion of the catheter. Manipulating the proximal portion may include attaching a syringe to a connector of a cover of the proximal portion of the catheter to expel fluid from the distal portion of the catheter. Manipulating the proximal portion may include extending a plunger that extends from the proximal portion of the catheter to expel fluid from the distal portion of the catheter.

In some aspects, the method includes filling the distal portion with fluid before positioning the distal portion of the catheter adjacent the target location within the patient. Filling the distal portion with fluid may include drawing fluid into the distal portion by creating a vacuum within the passage.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Figure 1:
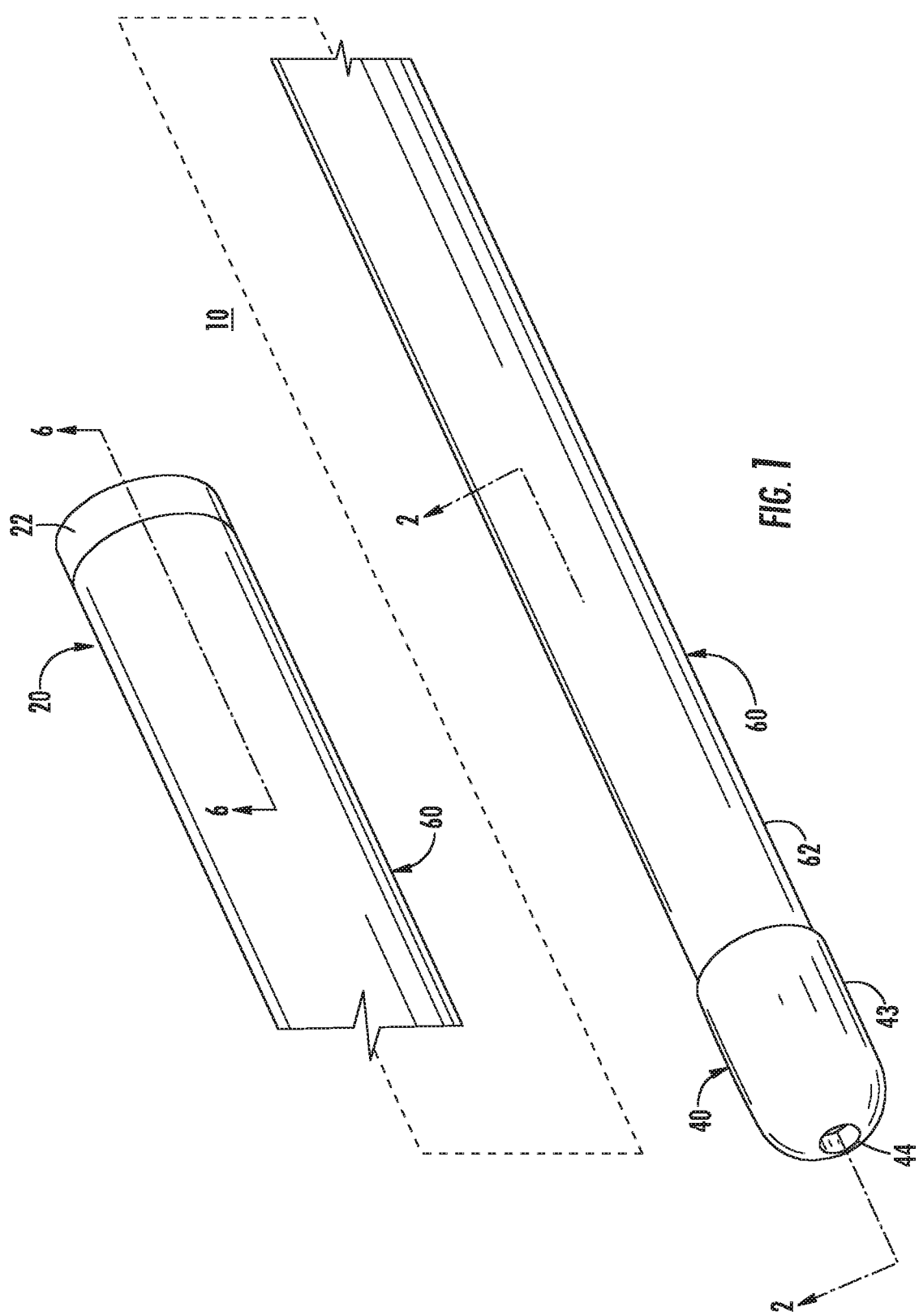
FIG. 1 is a perspective view of an exemplary fluid dispensing catheter provided in accordance with the present disclosure.

This disclosure relates generally to a fluid dispensing catheter for providing fluid to a remote location within the body in a controlled manner. The catheter includes a distal portion including a plug that restricts flow through a passage defined by the catheter. The catheter may include a tip that defines an opening. The tip may be shaped to atraumatically advance through tissue while allowing fluid to selectively flow from the tip in a controlled manner.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

Referring to FIG. 1, an exemplary fluid dispensing catheter 10 is described in accordance with the present disclosure. The catheter 10 includes a proximal portion 20, a distal portion 30, and an elongate body 60 between the proximal and distal portions 20, 30. The proximal portion 20 is configured to be disposed external to a patient and is engagable by a clinician to manipulate the distal portion 30. The distal portion 30 is configured to be inserted through a bronchoscope 390 (FIG. 9) and/or an extended working channel 96 (FIG. 9) to dispense fluid at a target site as described in detail below. The elongate body 60 passes through the bronchoscope 390 and/or extended working channel 96 to allow a clinician interfacing with the proximal portion 20 to dispense fluid from the distal portion 30 in a controlled manner.

Figure 2:
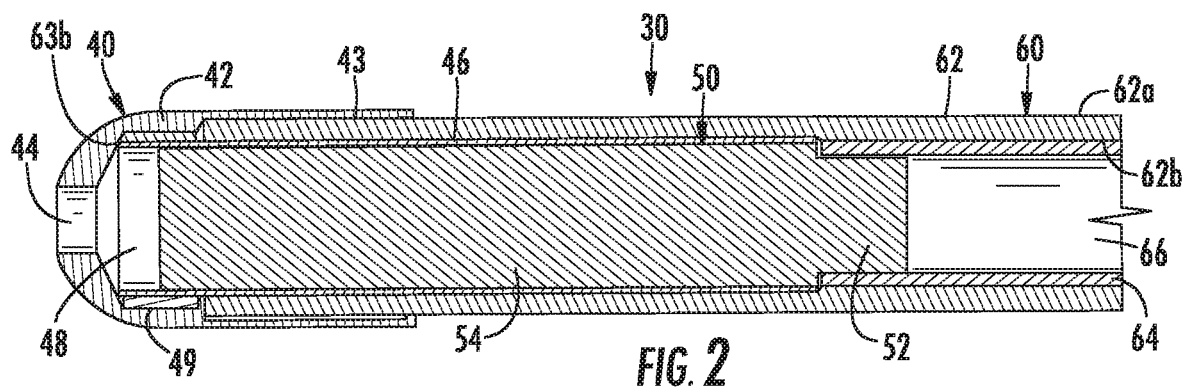
FIG. 2 is a cross-sectional view taken along section line 2-2 of FIG. 1.

With reference to FIG. 2, the elongate body 60 is formed from an outer member 62 having an outside surface 62a, an inside surface 62b, and an inner member 64 that defines a passage 66. The inner member 64 is flexible and configured to keep the passage 66 open such that the inner member 64 allows the elongate body 60 to bend, flex, and/or stretch while preventing the passage 66 from collapsing. The inner member 64 is disposed within and in substantial contact with the inside surface 62b of the outer member 62. As shown, the outer member 62 formed from a plastic material and the inner member 64 is a stainless steel coil disposed within the outer member 62. It is envisioned that the inner member 64 can be disposed between the outside and inside surfaces 62a, 62b of the outer member 62. Additionally or alternatively, the inner member 64 can be formed from a stainless steel coil and the outer member 62 can be formed from a coating applied over the stainless steel coil to substantially seal the coil. It is also envisioned that the elongate body 60 can include the inner member 64 without the outer member 66.

Figure 3:
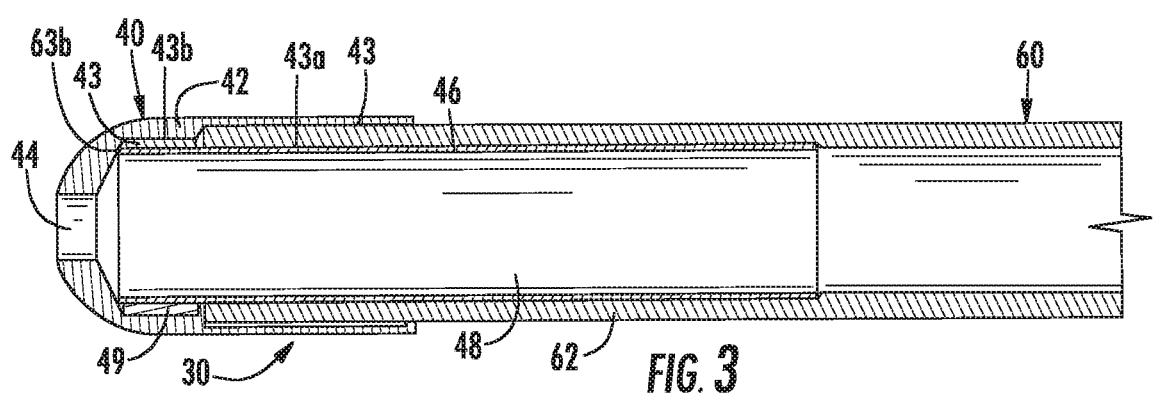
FIG. 3 is the cross-sectional view of FIG. 2 with a plug and an inner member removed.
Figure 4:
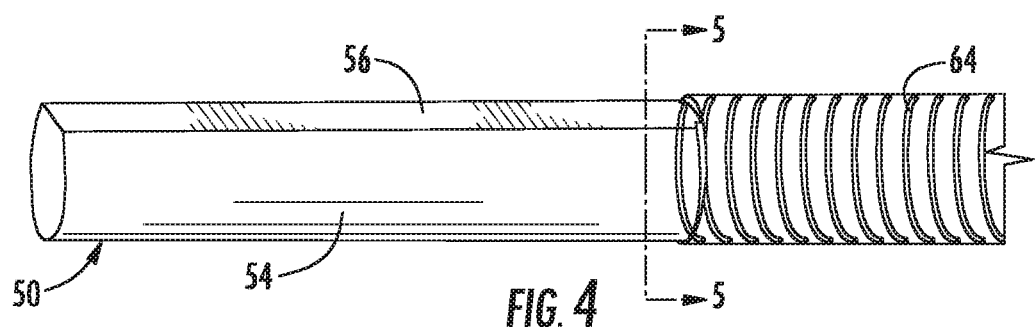
FIG. 4 is a perspective view of the plug and the inner member of FIG. 2.

Referring now to FIGS. 2-4, the distal portion 30 includes a tip 40 and a plug 50. The tip 40 includes a cap 42 and an inner wall 46. The cap 42 and the inner wall 46 define a channel 43 therebetween. As shown, the channel 43 is a stepped annular channel with a large dimension proximal portion 43a and a small diameter distal portion 43b; however, it is contemplated that the channel 43 can have a constant dimension. The tip 40 is disposed over a distal end 63b of the outer member 62 with the distal end 63b captured within the channel 43 such that the tip 40 is secured to the distal end 63b. When the distal end 63b of is captured within the channel 43, the inner wall 46 is disposed within the outer member 62. The inner wall 46 defines a tip passage 48 that is in communication with the passage 66. The cap 42 defines a tip opening 44 that is in communication with the tip passage 48. The tip 40 has an arcuate distal end portion such that the tip 40, and the catheter 10, can be atraumatically advanced through a bronchoscope, extended working channel, and/or body lumen.

Figure 5:
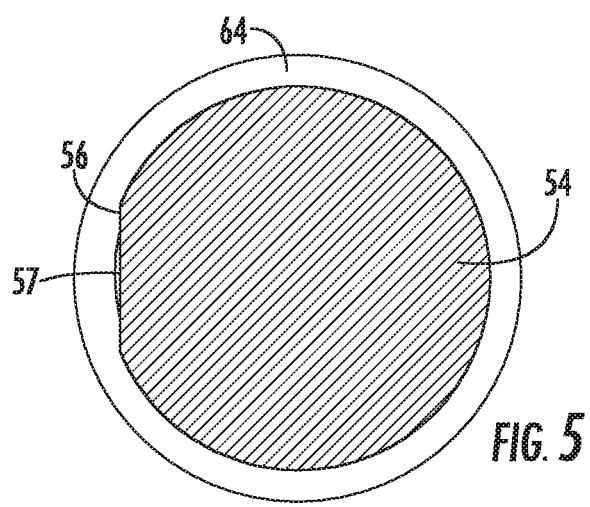
FIG. 5 is a cross-sectional view taken along section line 5-5 of FIG. 4.

With additional reference to FIG. 5, the plug 50 includes a proximal cylinder section 52 disposed within the passage 66 and a distal cylinder section 54 disposed within the tip passage 48 of the inner wall 46. The plug 50 partially occludes the passage 66 and configured to restrict flow of fluid from the passage 66, through the tip passage 48, and out of the tip opening 44. The plug 50 also includes a flat 56 that defines a plane parallel to and offset from a longitudinal axis of the plug 50 and extends a length of the plug 50. It is envisioned that the flat 56 may extend the entire length of the proximal cylinder section 52 and only a portion of the distal cylinder section 54. The proximal cylinder section 52 has a diameter substantially equal to a diameter of the passage 66 with the flat 56 defining a gap 57 with the inner member 64 such that fluid flow from the passage 66 is restricted to flow through the gap 57. The proximal cylinder section 52 can be welded (e.g., laser welded) to the inner member 64. It will be appreciated that when the proximal cylinder section 52 is welded to the inner member 64, areas adjacent the flat 56 are not welded to maintain the dimension of the gap 57.

Figure 6:
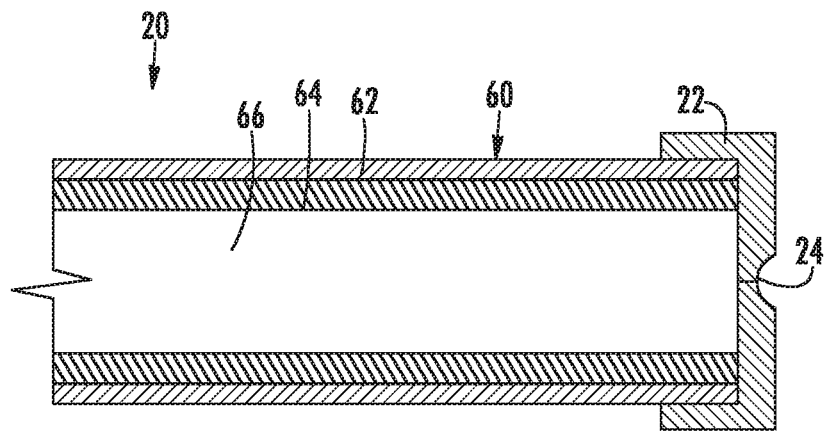
FIG. 6 is a cross-sectional view taken along section line 6-6 of FIG. 1.

Referring now to FIG. 6, the proximal portion 20 of the catheter 10 includes a cover 22 that seals the passage 66. The cover 22 can include a septum 24 that is configured to seal about a syringe 500 (FIG. 9) inserted through the septum 24.

Prior to use, the catheter 10 is filled or loaded with fluid to be delivered to target tissue. The fluid can be a therapeutic fluid, a visual marker fluid, an electromagnetic marker fluid, a fluoroscopic marker fluid, etc. To fill the catheter 10, the syringe 500 is filled with a desired fluid. The filled syringe 500 is then inserted through the septum 24 of the cover 22 and emptied into the passage 66. The fluid flows through the passage to the distal portion 30 of the catheter 10. The fluid may cover the gap 57 such that the passage 66 is sealed and the fluid is retained within the passage 66. The syringe 500 can be used to partially or entirely fill the passage 66.

Alternatively, the catheter 10 can be filled by inserting an empty syringe 500 through the septum 24 with the tip opening 44 disposed within the desired fluid. With the tip opening 44 in the desired fluid, the syringe 500 can be drawn to create a vacuum within the passage 66 to draw the desired fluid into the passage 66.

Figure 7:
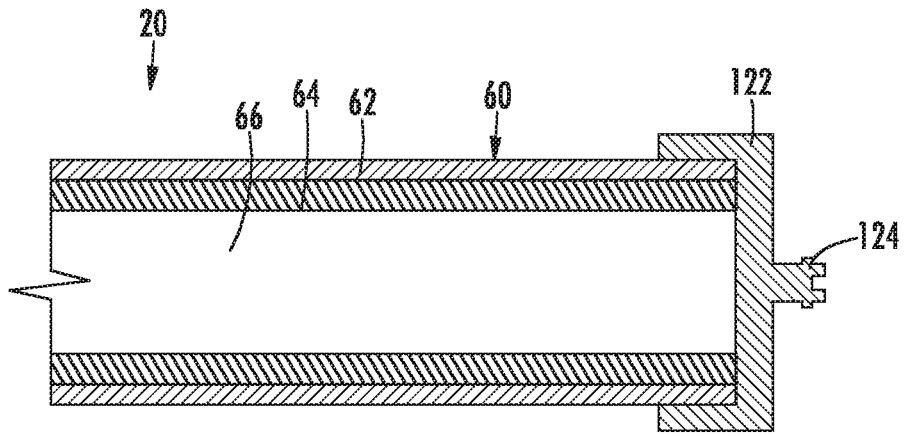
FIG. 7 is a cross-sectional view of another embodiment of a proximal portion of the catheter of FIG. 1.
Figure 8:
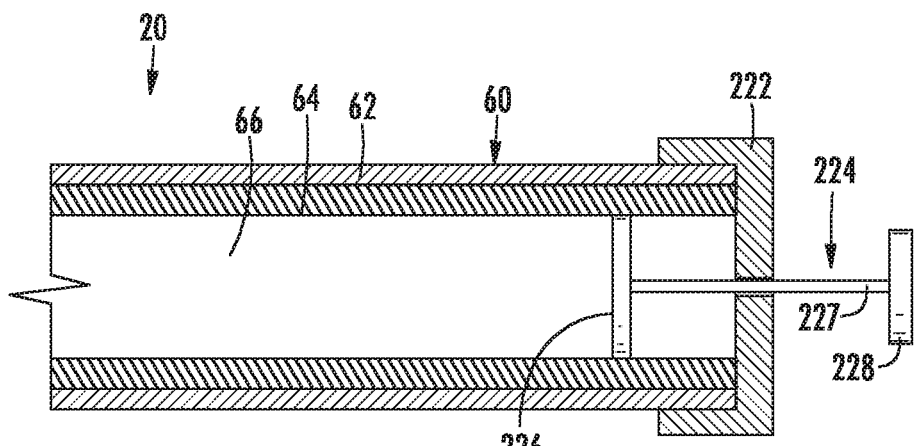
FIG. 8 is a cross-sectional view of yet another embodiment of a proximal portion of the catheter of FIG. 1.

With reference to FIGS. 7 and 8, the proximal portion 22 of the catheter 10 can include other structures for sealing the passage 66, filling the passage 66 with a desired fluid, and dispensing the desired fluid from the passage 66 in a controlled manner. For example, with reference to FIG. 7, the proximal portion 22 can include a cover 122 including a Luer connector 124 for sealingly attaching a syringe to the cover 122. The cover 122 functions substantially similar to the cover 22 and will not be described in detail for reasons of brevity. Alternatively, referring to FIG. 8, the proximal portion 20 can include a cover 222 having a plunger 224 having a disc 226 disposed within the passage 66, a handle 228, and a shaft 227 interconnecting the disc 226 and the handle 228. As the plunger 224 is drawn proximally within the passage 66, a vacuum is formed within the passage 66 to draw fluid into the distal portion 30 of the catheter 10 and when the plunger 66 is extended distally within the passage 66, pressure is increased within the passage 66 such that fluid is expelled from the passage 66 in a similar manner to the syringe detailed above.

Figure 9:
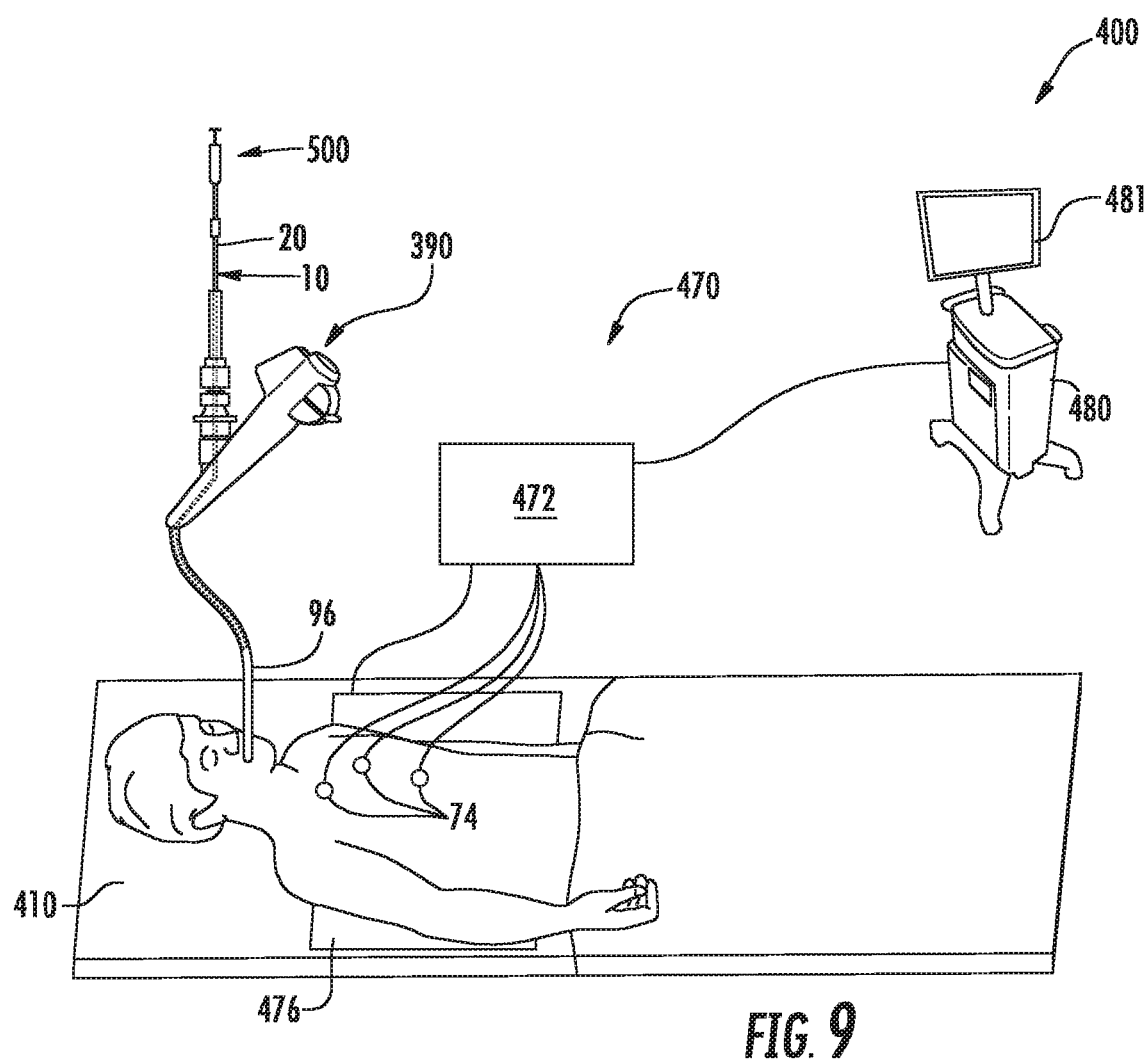
FIG. 9 is a perspective view of an exemplary surgical system including the fluid dispensing catheter of FIG. 1.

With reference to FIG. 9, an electromagnetic navigation (EMN) system 400 is provided in accordance with the present disclosure to position the tip 40 (FIG. 1) of the filled catheter 10 adjacent target tissue. FIG. 9 also depicts the fluid dispensing catheter 10 for use with the EMN system 400. One such EMN system is the ELECTROMAGNETIC NAVIGATION BRONCHOSCOPY® system currently sold by Covidien LP. Among other tasks that may be performed using the EMN system 400 are planning a pathway to target tissue, navigating a catheter guide assembly to the target tissue, deploying an instrument adjacent or into the target tissue to treat or capture the target tissue, digitally marking the location of the target tissue in a data file related to the planned pathway, and placing one or more echogenic markers at or around the target tissue.

The EMN system 400 generally includes an operating table 410 configured to support a patient; a bronchoscope 390 configured for insertion through the patient's mouth and/or nose into the patient's airways; a tracking system 470 including a tracking module 472, a plurality of reference sensors 474, and an electromagnetic field generator 476; and a workstation 480 including software and/or hardware used to facilitate pathway planning, identification of target tissue, navigation to target tissue, and digitally marking the biopsy location.

The EMN system 400 is used to position an extended working channel (EWC) 96 adjacent target tissue. The EMN system 400 may include a locatable guide (LG) catheter (not shown) to position the EWC 96. An example of a similar catheter guide assembly is currently marketed and sold by Covidien LP under the name EDGE™ Procedure Kits. For a more detailed description of the use of the catheter guide assembly reference is made to commonly-owned U.S. Patent Publication 2016/0000302, the entire contents of which are hereby incorporated by reference. Alternatively, the tip 40 of the catheter 10 can include a sensor 49 (FIG. 2), visible to the EMN system 400, that can be used to position the EWC 96 adjacent target tissue.

With the EWC 96 positioned adjacent target tissue, the tip 40 of the catheter 10 is passed through the EWC 96 until the tip 40 extends from the EWC 96. Fluoroscopy can be used to confirm the location of the tip 40. With the tip 40 extended from the EWC 96, a syringe 500 filled with a fluid (e.g., saline, oxygen, air, therapeutic fluid, marking fluid, etc.) is inserted through the cover 22. The syringe 500 is then extended to increase pressure within the passage 66 of the catheter 10. As the pressure within the passage 66 is increased, the desired fluid in the distal portion 30 of the catheter 10 flows through the gap 57 and out the tip opening 44 of the catheter 10. The small size of the gap 57 controls the rate at which the desired fluid is dispensed from the tip opening 44. The amount of desired fluid dispensed can be determined by the amount of fluid expelled from the syringe 500. For example, when the passage 66 is filled with a substantially uncompressible fluid and the syringe 500 is filled with saline or a similar uncompressible fluid, the amount of fluid dispensed will be substantially equal to the amount of fluid expelled from the syringe 500.

While the use of the catheter 10 is detailed herein for use in the airway of a patient, it is contemplated that the catheter 10 may be used in a variety of surgical procedures utilizing elongated surgical instruments with extended working channels. For example, the catheter 10 may be used during various endovascular procedures such as cardiac interventions, general vascular interventional procedures, cerebral interventions, etc. These procedures may include, but are not limited to, balloon dilations, stent placements, percutaneous valve replacement, percutaneous valve repair, pacing lead placement, cardiac ablation procedures, and electrical mapping procedures.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto.

What is claimed is:

1. A fluid dispensing catheter, comprising:
   an inner member defining a first passage;
   an outer member extending distally past the inner member and defining a second passage, the inner member disposed within the second passage;
   an opening defined at a distal end portion of the fluid dispensing catheter and configured to dispense a fluid to target tissue; and
   a plug having a proximal section positioned within the first passage and a distal section extending distally from the proximal section, the distal section positioned outside of the first passage and within the second passage, the plug configured to control a flow of the fluid through the opening.

2. The fluid dispensing catheter according to claim 1, wherein the proximal section of the plug is positioned within the first passage at the distal portion of the inner member to at least partially occlude the first passage.

3. The fluid dispensing catheter according to claim 1, wherein the plug includes a flat disposed parallel to and offset from a longitudinal axis defined by the plug, the flat defining a gap configured to control a flow of the fluid through the first passage.

4. The fluid dispensing catheter according to claim 1, wherein the proximal section of the plug has a first diameter and the distal section of the plug has a second diameter larger than the first diameter.

5. The fluid dispensing catheter according to claim 1, wherein the opening is defined through a cap disposed over a distal portion of the outer member, and the opening is in fluid communication with the first passage.

6. The fluid dispensing catheter according to claim 1, wherein a proximal portion of the inner member includes a cover configured to fluidly seal the first passage.

7. The fluid dispensing catheter according to claim 6, wherein the cover includes a septum configured to form a fluid seal about a medical instrument inserted through the septum for delivering fluid to the first passage.

8. The fluid dispensing catheter according to claim 6, wherein the cover includes a Luer connector for fluidly coupling a medical instrument to the first passage.

9. The fluid dispensing catheter according to claim 6, further comprising a plunger coupled to the cover, the plunger configured to at least one of draw fluid into the first passage or expel fluid from the first passage.

10. The fluid dispensing catheter according to claim 1, wherein the first passage is defined between a proximal portion of the inner member and a distal portion of the inner member.

11. A fluid dispensing catheter, comprising:
    an inner member defining a first passage configured to receive fluid;
    an outer member defining a second passage, the inner member disposed within the second passage;
    an opening defined at a distal end portion of the fluid dispensing catheter and configured to receive the fluid from the first passage for delivery of the fluid to target tissue; and
    a plug having a proximal section and a distal section extending distally from the proximal section, the distal section positioned outside of the first passage and within the second passage.

12. The fluid dispensing catheter according to claim 11, wherein the outer member extends distally past the inner member.

13. The fluid dispensing catheter according to claim 11, wherein the proximal section of the plug is positioned within the first passage at a distal portion of the inner member to at least partially occlude the first passage.

14. The fluid dispensing catheter according to claim 11, wherein the plug includes a flat disposed parallel to and offset from a longitudinal axis defined by the plug, the flat defining a gap configured to control a flow of the fluid through the first passage.

15. A fluid dispensing catheter, comprising:
    an inner member defining a first passage configured to receive fluid;
    a cover coupled to the inner member and configured to fluidly seal the first passage;
    an outer member defining a second passage, the inner member disposed within the second passage;
    an opening defined at a distal end portion of the fluid dispensing catheter and configured to receive the fluid from the first passage for delivery of the fluid to target tissue; and
    a plug having a proximal section and a distal section, the distal section positioned outside of the first passage and within the second passage.

16. The fluid dispensing catheter according to claim 15, wherein the outer member extends distally past the inner member.

17. The fluid dispensing catheter according to claim 15, wherein the proximal section of the plug is positioned within the first passage at a distal portion of the inner member to at least partially occlude the first passage.

18. The fluid dispensing catheter according to claim 15, wherein the cover includes a septum configured to form a fluid seal about a medical instrument inserted through the septum for delivering fluid to the first passage.

19. The fluid dispensing catheter according to claim 15, wherein the cover includes a Luer connector for fluidly coupling a medical instrument to the first passage.

20. The fluid dispensing catheter according to claim 15, further comprising a plunger coupled to the cover, the plunger configured to at least one of draw fluid into the first passage or expel fluid from within the first passage.

\* \* \* \* \*